(12) United States Patent
Higuchi (10) Patent No.: US 6,475,776 B1
(45) Date of Patent: Nov. 5, 2002

(54) INCUBATOR, AND METHOD FOR MAKING ATMOSPHERE UNIFORM IN INCUBATOR STORAGE BOX

(75) Inventor: Akira Higuchi, Fukuoka (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 54 days.

(21) Appl. No.: 09/595,585

(22) Filed: Jun. 15, 2000

(30) Foreign Application Priority Data

Jun. 23, 1999 (JP) .............................................. 11-176461

(51) Int. Cl.$^7$ ................................................. C12M 1/02
(52) U.S. Cl. .................... 435/303.3; 435/809; 422/104; 422/99
(58) Field of Search ........................... 435/303.1, 303.3, 435/809; 422/104.99; 312/1, 35, 43, 236

(56) References Cited

U.S. PATENT DOCUMENTS 5,470,744 A * 11/1995 Astle
6,228,636 B1 * 5/2001 Yahiro et al.

FOREIGN PATENT DOCUMENTS

| EP | 0 339 824 A1 | * 11/1989 |
| JP | 11-313666 A | * 11/1999 |
| JP | 2000-37184 A | * 2/2000 |

* cited by examiner

Primary Examiner—William H. Beisner
(74) Attorney, Agent, or Firm—RatnerPrestia (57) ABSTRACT

Even in a case of an incubator having a sample rack of complicated shape, the internal environmental condition in the incubator is maintained uniformly, so that the reliability of biochemical treatment can be assured. It includes a storage box, the sample rack movably disposed in the storage box, a moving device for moving the sample rack, and a controller for controlling the moving device. The controller has a function of selectively controlling the positioning operation for positioning the sample rack at specified positions, and the agitating operation for moving the sample rack, and by the agitating operation for moving the sample rack, the atmosphere in the storage box is agitated to be uniform. Preferably, the sample rack has a plurality of sample tables coupled in the longitudinal direction.

9 Claims, 6 Drawing Sheets

INCUBATOR, AND METHOD FOR MAKING ATMOSPHERE UNIFORM IN INCUBATOR STORAGE BOX

TECHNICAL FIELD OF THE INVENTION

The present invention relates to an incubator, more particularly to an incubator and a method for making the atmosphere uniform in an incubator storage box used in culture of cells and microorganisms.

BACKGROUND OF THE INVENTION

The incubator is known as an apparatus used in culture of microorganisms and cells, and biochemical process such as biochemical reaction. The incubator comprises a storage box for containing samples of culture and test, and a function of maintaining the environmental conditions such as temperature and humidity in the storage box. Generally, for the purpose of processing multiple samples in same environmental conditions, multiple samples are put in the incubator. For example, multiple layers of sample racks are placed in the storage box, and multiple samples are put on multiple racks. These samples must be kept in uniform environmental conditions, and the conventional incubators had blowers and other air agitating means in the storage box in order to distribute temperature and humidity uniformly inside.

However, the conventional agitation by blowing air was not sufficient in the agitating effect in the incubator comprising multiple layers of sample racks in order to contain as many samples as possible in the storage box of a limit volume. It is because the draft effect by a simple draft fan hardly permeates deeply into narrow gaps. With the conventional incubator, therefore, it is difficult to maintain the internal environmental conditions uniformly and the reliability of biochemical processing is not assured.

It is hence an object of the invention to present an incubator capable of maintaining the internal environmental conditions uniformly and having an excellent reliability.

SUMMARY OF THE INVENTION

A incubator of the invention comprises a storage box, a sample rack movably disposed in the storage box, a moving device for moving the sample rack, and a controller for controlling the moving device. The controller has a function of selectively controlling the positioning operation for positioning the sample rack at predetermined positions, and the agitating operation for agitating the atmosphere in the storage box uniformly by moving the sample rack.

A method for making the atmosphere uniform in the incubator storage box of the invention comprises (a) a step of supplying the incubator, in which the incubator comprises the storage box, and a sample rack is movably disposed in the storage box and moving device for moving the sample rack, (b) a step of putting samples on the sample rack, (c) a step of setting the atmosphere in the storage box in a predetermined environment, and (d) a step of agitating the atmosphere in the storage box by moving the sample rack.

In this constitution, the environmental condition in the incubator is agitated to be uniform. In particular, if the incubator has multiple sample racks with complicated shapes, the environmental condition in the incubator can be maintained uniformly.

REFERENCE NUMERALS

1 Incubator
2 Housing
2a First opening
2b Second opening
2e First space
2f Second space
33 Door
5 Shutter
6 Plate
9 Cylinder
10 Sample rack
11 Sample table
11a Circular hole
11b Platform
12 Slide guide
12a Slider
13 Feed screw
14 Nut
15 Spline shaft
16 Coupling member
17 Rotating element
18 Elevating element
19 Partition wall
19a Bearing
19b Bearing
20 R-axis motor
20a R-axis encoder
20b R-axis counter
22 Pulley
23 Belt
24 Belt
25 Z-axis motor
25a Z-axis encoder
25b Z-axis counter
27 Pulley
28 Pulley
29 Belt
41 Motor drive unit
42 Environment controller
43 First communication unit
50 Controller
53 Second communication unit

DETAILED DESCRIPTION OF THE INVENTION

Figure 1:
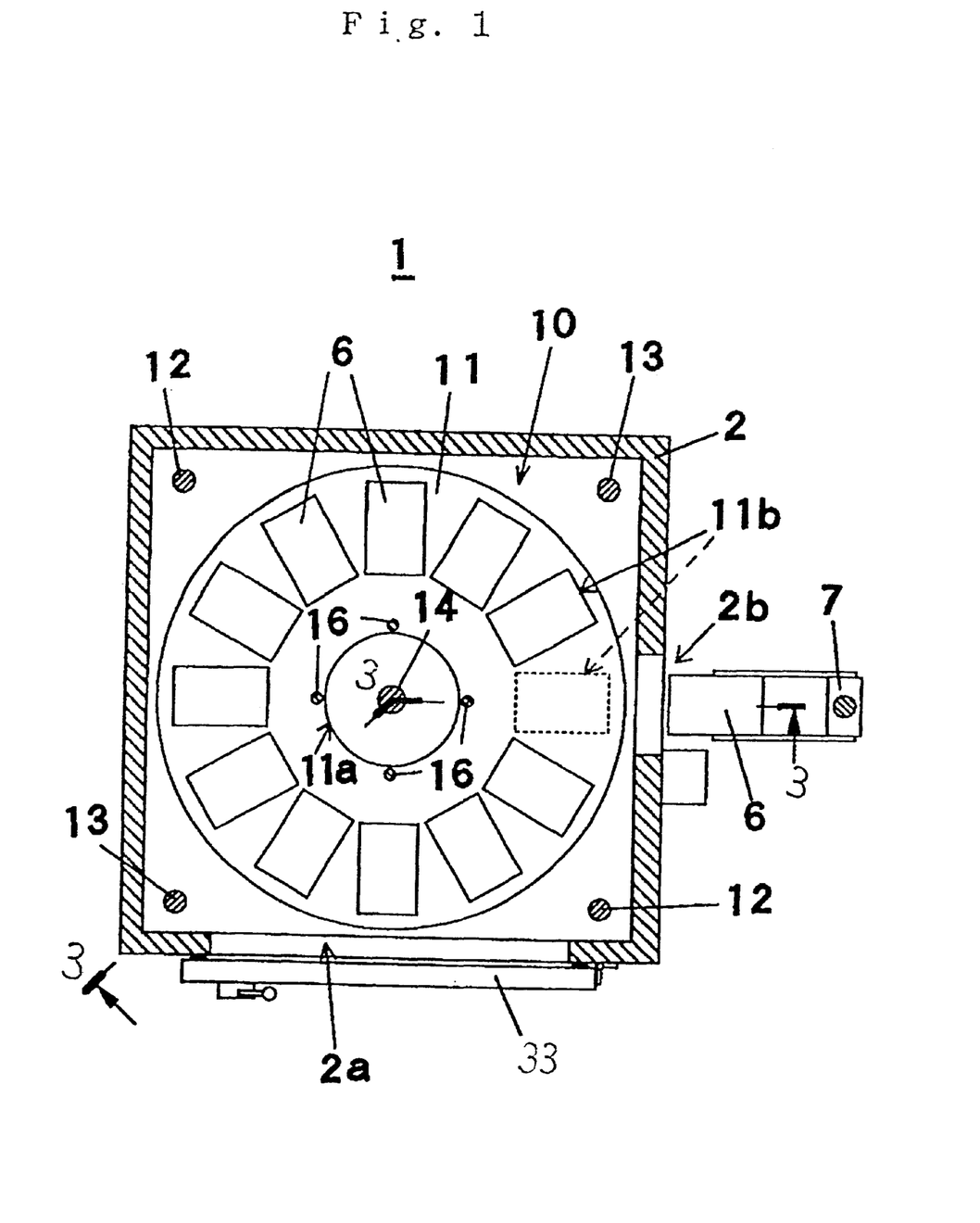
FIG. 1 is a plane sectional view of an incubator in an embodiment of the invention.
Figure 2:
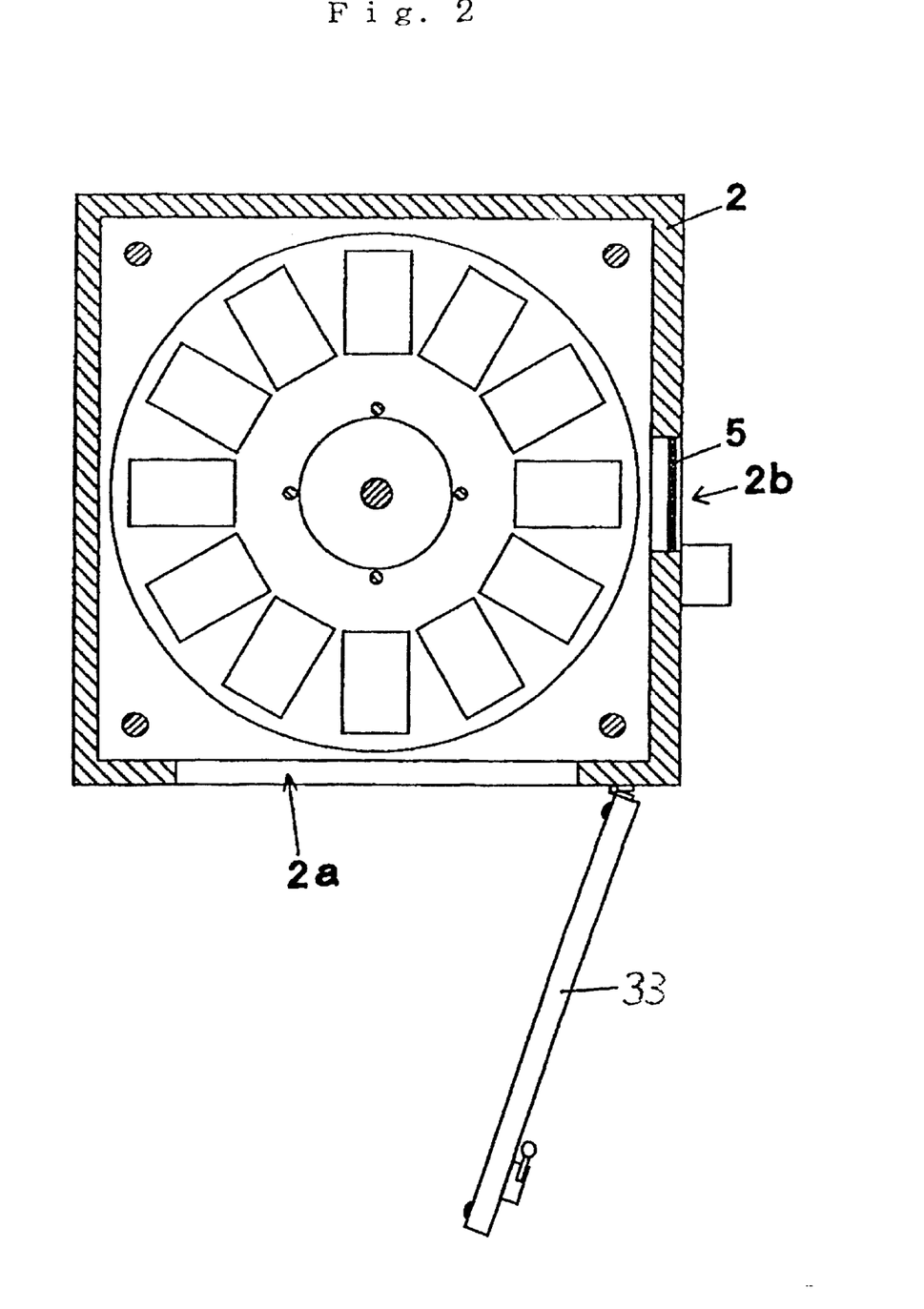
FIG. 2 is a plane sectional view of an incubator in other embodiment of the invention.
Figure 3:
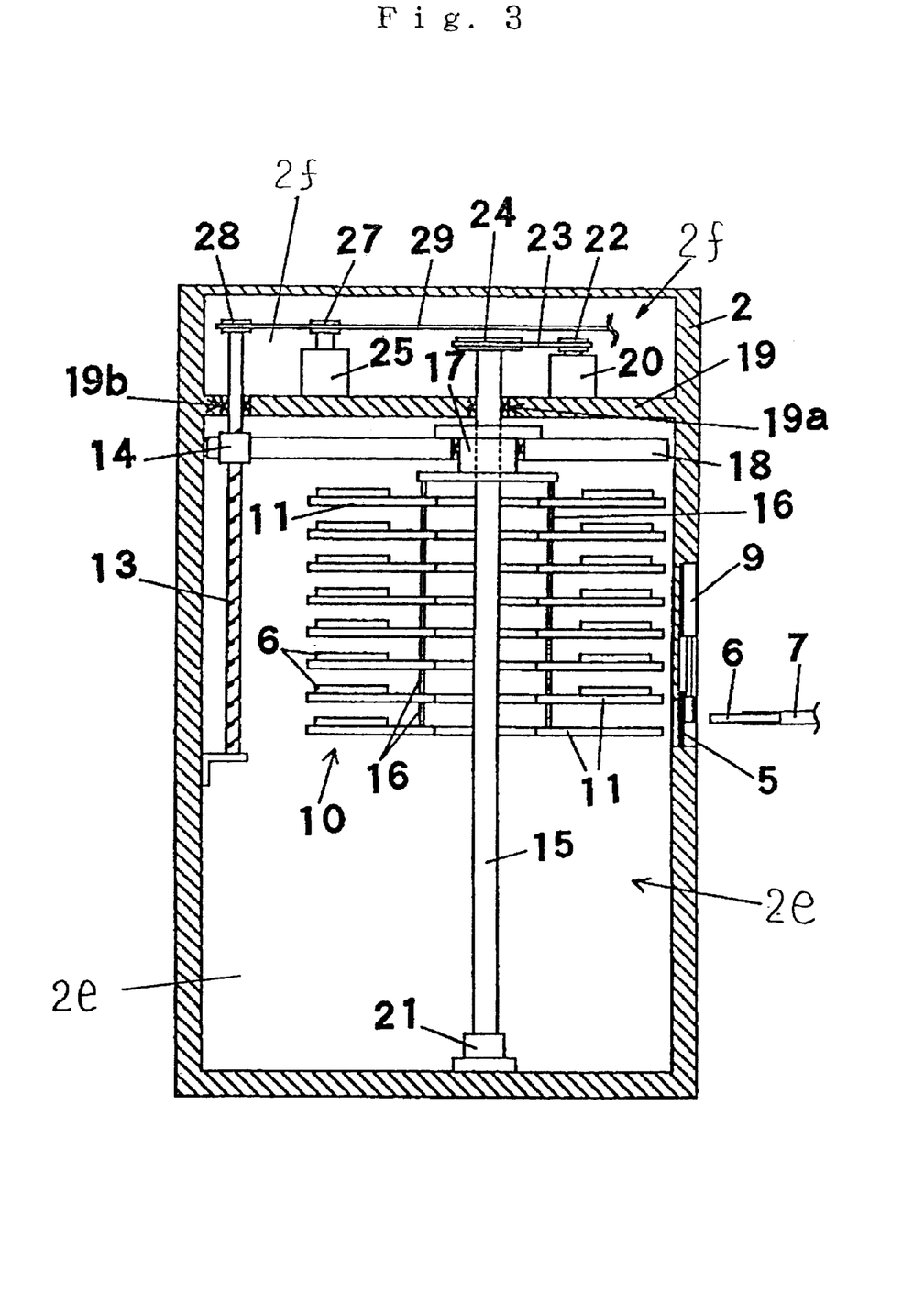
FIG. 3 is a side view of the incubator in the embodiment of the invention.

Referring now to the drawings, preferred embodiments of the invention are described below. Plane sectional views of incubator in embodiments of the invention are shown in FIG. 1 FIG. 2. A side sectional view of the incubator is shown in FIG. 3. The internal see-through view of the incubator is given in FIG. 4. The structure of the control system of the incubator is shown in a block diagram in FIG. 5.

Referring to FIG. 1 and FIG. 2, the internal structure of the incubator is explained. In FIG. 1, an incubator 1 has a housing 2 of heat insulating walls. The housing 2 incorporates a water jacket (not shown). Internal environmental conditions of the housing 2, such as temperature, humidity, carbon dioxide concentration, and other gas concentration are controlled by an environment controller (not shown) so as to maintain specified conditions.

A first opening 2a is provided at the front side of the housing 2. The first opening 2a is opened and closed by a first door 3. A second opening 2b is provided at the side of the housing 2. The second opening 2b is large enough for passing at least one plate 6 which is a sample container, and is used as a plate access. A shutter 5 which is a second door opening and closing in the vertical direction is provided in the second opening 2b. The shutter 5 is opened and closed automatically in the vertical direction by means of a cylinder 9 (see FIG. 5) used as a driving device. In FIG. 3, a door 33 is opened, the first opening 2a is opened, and the second opening 2b is closed by the shutter 5. A conveying device 7 conveys the necessary container 6 to and from a dispensing device (not shown) through the second opening 2b.

Figure 4:
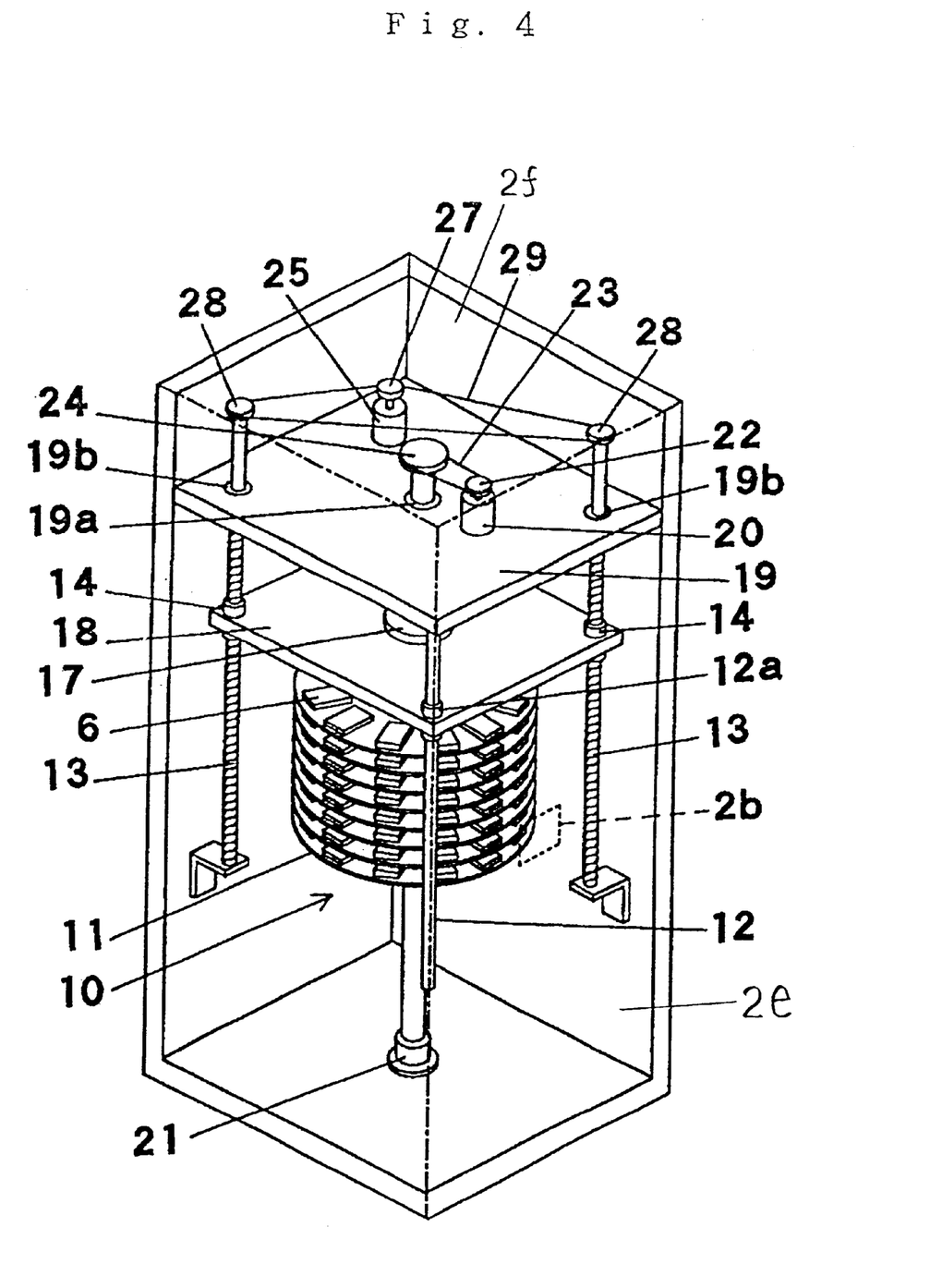
FIG. 4 is an internal see-through view of the incubator in the embodiment of the invention.

Referring to FIG. 3 and FIG. 4, the internal structure of the housing 2 is explained. Sample racks 10 coupling a plurality of layers of circular sample tables 11 are disposed in the housing 2. As shown in FIG. 1, the sample table 11 is an annular member having a circular hole 11 formed in the center. A plurality of platforms 11b (twelve platforms in this embodiment) for mounting plates 6 are disposed radially on the principal plane of the sample tables 11. The plates 6 are put on the platforms 11b. Each platform 11b is identified with an individual number. A specific platform 11b is identified by this number by man or controller.

FIG. 3 is a sectional view along line 3—3—3 in FIG. 1. As shown in FIG. 3 and FIG. 4, the inside of the housing 2 is divided into a first space 2e and a second space 2f by means of a horizontal partition wall 19. The first space 2e below the partition wall 19 functions as a storage box for accommodating samples for biochemical process in a controlled environment. The second space 2f above the partition wall 19 is a power house incorporating a driving mechanism. The driving mechanism has a function of driving the sample racks 10 disposed in the first space 2e. The second space 2f is closed, or an open space free from ceiling and four side walls.

The sample racks 10 couple the plurality of sample tables 11 vertically by means of coupling members. The sample table 11 of the highest layer is coupled to a rotating element 17 rotatably supported on an elevating member 18 through the coupling member 16. A spline shaft 15 disposed vertically is slidably inserted into the rotating element 17. The lower end of the spline shaft 15 is supported by a bearing 21 disposed at the bottom of the housing 2. The upper part of the spline shaft 15 is supported on a bearing 19a provided in the shaft hole formed in the partition wall 19, and projects into the second space 2f. A pulley 24 is coupled to the upper end of the spline shaft 15.

A pulley 22 is coupled to an R-axis motor 20 disposed on the top of the partition wall 19. A belt 23 is stretched between the pulley 22 and the pulley 24. By driving the R-axis motor 20, the spline shaft 15 rotates. When this rotation is transmitted to the rotating element 17, the sample racks 10 make rotary motions together with the spline shaft 15. Therefore, the R-axis motor 20, pulley 22, belt 23 and pulley 24 rotate the sample racks 10 by rotating the spline shaft 15, thereby composing a rotary drive mechanism.

Two nuts 14 (only one shown in FIG. 3) are coupled to two diagonal positions of the elevating member 18. A feed screw 13 is driven into the two nuts 14 in the vertical direction. The feed screw 13 is supported on the bearing 19b fitted in the shaft hole formed in the partition wall 19, and projects into the second space 2f. A pulley 28 is coupled to the upper end of the feed screw 13. A pulley 27 is coupled to a Z-axis motor 25 disposed on the partition wall 19. A belt 29 is stretched between the pulley 27 and the pulley 28.

Sliders 12a (only one shown in FIG. 4) slidably engaged with two slide guides 12 (see FIG. 1) are mounted on the elevating member 18. The elevating motion of the elevating member 18 is guided by the slide guides 12 and sliders 12a. By driving the motor 25, the feed screw 13 rotates and the elevating member 18 moves up and down. Therefore, the Z-axis motor 25, pulley 27, pulley 28 and belt 29 function as an elevating drive mechanism for rotating the feed screw 13.

That is, in this constitution, the spline shaft 15 and feed screw 13 are respectively coupled to the rotary drive mechanism and elevating drive mechanism through the bearings 19a, 19b provided in the partition wall 19. As a result, the drive mechanism can be disposed in the second space 2f. That is, the second space 2f is isolated from the first space 2e generally in the atmosphere of high temperature and high humidity, and the drive mechanism such as motors installed in the second space 2f is isolated and protected from the environments of high temperature and high humidity.

Along with the elevating motion of the elevating member 18, the sample racks 10 also ascend and descend. At this time, the sample racks 10 can be rotated by the spline shaft 15 at any position in the vertical direction, so that the sample racks 10 move in combination of rotary motion and elevating motion. The rotary drive mechanism and elevating drive mechanism compose a moving mechanism for moving the sample racks 10. In this moving operation, by counting the pulse signals generated from the encoders built in the R-axis motor 20 and Z-axis motor 25, the present position of each platform 11b is identified.

Figure 5:
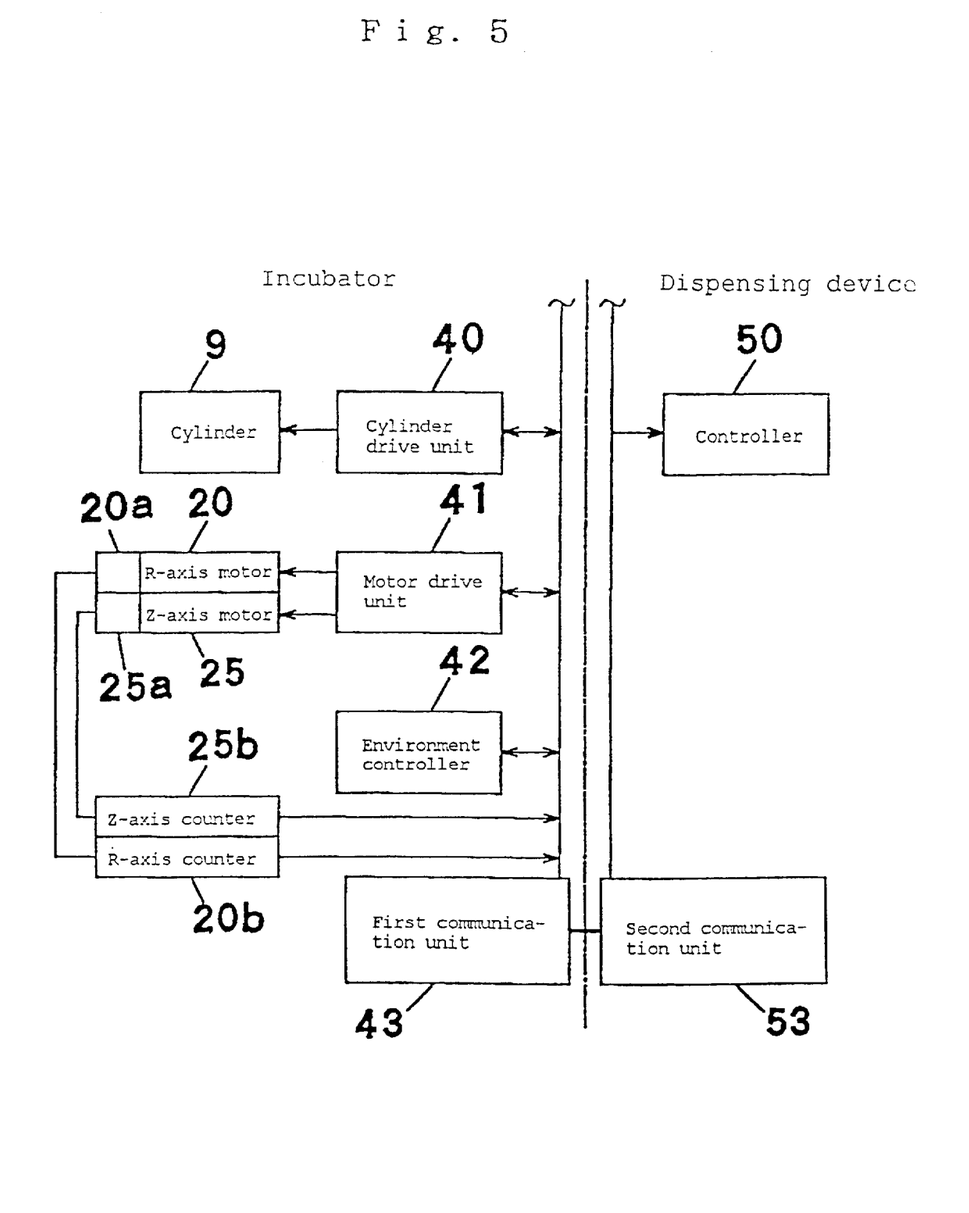
FIG. 5 is a block diagram showing a configuration of control system of the incubator in the embodiment of the invention.

Referring next to FIG. 5, the control system of the incubator 1 is explained. A cylinder drive unit 40 drives the cylinder 9. The cylinder 9 moves the shutter 5 up and down. The shutter 5 opens and closes the plate access 4. A motor drive unit 41 drives the R-axis motor 20 and Z-axis motor 25. The R-axis motor 20 rotates the sample racks 10. The Z-axis motor 25 elevates the elevating member 18. An encoder 20a is built in the R-axis motor 20. This encoder 20a issues pulse signals by detecting the rotation of the rotary shaft of the R-axis motor 20. The pulse signals are counted by an R-axis counter 20b. An encoder 25a is built in the Z-axis motor 25. This encoder 25a issues pulse signals by detecting the rotation of the rotary shaft of the Z-axis motor 25. The pulse signals are counted by a Z-axis counter 25b.

The counts by the R-axis counter 20b and Z-axis counter 25b are referred to as the information for identifying the position of the platform 11b. In this embodiment, the R-axis encoder 20a, R-axis counter 20b, Z-axis encoder 25a and Z-axis counter 25b function as the position detecting device for detecting the position of the sample rack. As the position detecting device, aside from the encoders built in the motors, a position detecting device for detecting directly the position of the sample rack 10, and a detector for detecting the motion of the sample rack 10 and issuing a pulse signal may be also used.

An environment controller 42 holds the internal environmental conditions in the housing 2, such as temperature, humidity and carbon dioxide concentration. A first communication unit 43 exchanges signals necessary for control of parts of the incubator 1. A controller 50 is disposed in a dispensing device, not shown, used in combination with the incubator 1. The first communication unit 43 of the incubator 1 exchanges signals through a second communication unit 53 of the dispensing device. The controller 50 controls the operation of the parts of the incubator 1 through the first communication unit 43.

The controller 50 commands door opening and closing operation to the cylinder drive unit 40. By the command from the controller 50, when discharging the plate 6 on the sample platform 11b to outside of the incubator 1, the plate access 4 is opened or closed. The controller 50 refers to the counts of the R-axis counter 20b and Z-axis counter 25b, and identifies the position of the platform 11b (for example, the number of the platform positioned before the second opening 2b). The controller 50 further commands positioning of the sample racks 10 or agitation to the motor drive unit 41.

That is, by controlling the motor drive unit 41, an arbitrary platform 11b can be positioned at a specific position, or the sample racks 10 are agitated by combination of elevating motion and rotary motion. The specific position is, for example, a position capable of picking up a plate 6 on the platform 11b through the second opening 2b by means of the conveying device 7. This agitating motion has the function of positioning and agitating the internal atmosphere of the first space 2e. As the sample racks 10 move at least by elevating or rotating, the internal atmosphere of the first space 2e which is the environmental control chamber of the incubator 1 is agitated, and the temperature and humidity are made uniform. That is, for the purpose of making uniform the temperature and humidity by agitating the internal atmosphere of the first space 2e which is the environmental control chamber of the incubator 1, positioning motion or agitating motion is selectively executed by the command from the controller 50. Therefore, the controller 50 functions as a control device for controlling the moving device for moving the sample racks 10.

The operation and method of the incubator are explained below.

Figure 6:
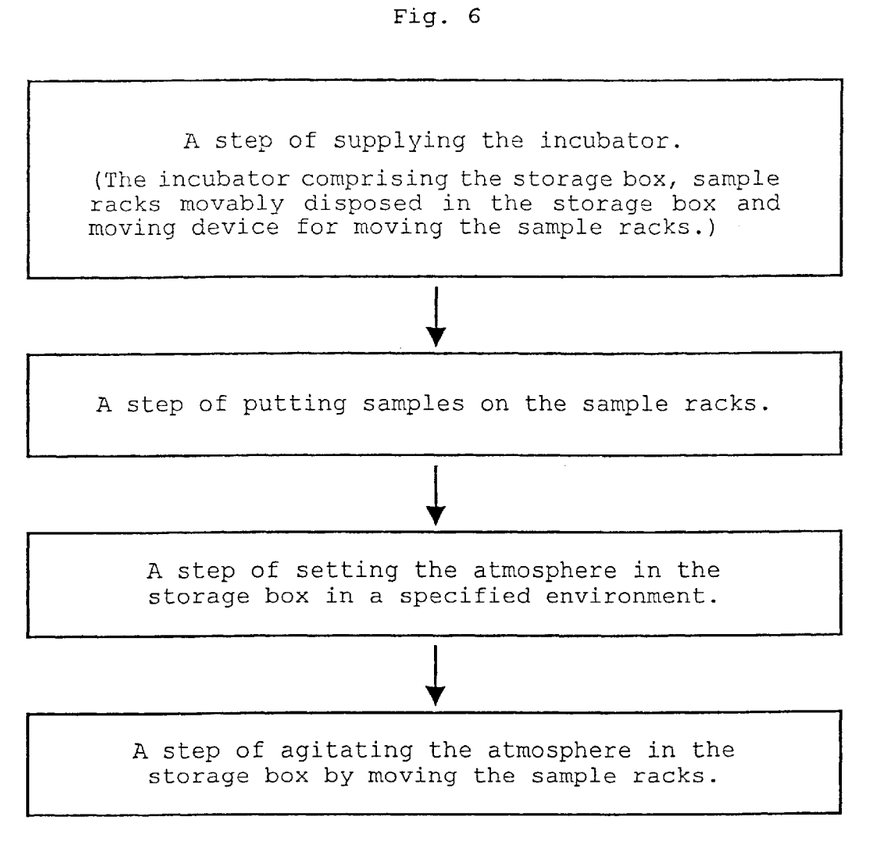
FIG. 6 is a schematic process chart of a method of making the atmosphere uniform in a storage box of the incubator in the embodiment of the invention.

As shown in FIG. 6, the method for making uniform the atmosphere in the storage box of the incubator roughly comprises:

(a) a step of supplying the incubator, in which the incubator comprises the storage box, sample racks are movably disposed in the storage box and moving device for moving the sample racks, (b) a step of putting samples on the sample racks, (c) a step of setting the atmosphere in the storage box in a specified environment, and (d) a step of agitating the atmosphere in the storage box by moving the sample racks.

The operation of the incubator is described while referring to FIG. 1 to FIG. 6. Prior to start of biochemical process, the plates 6 are set in the incubator 1. In this setting process, the plates 6 holding specified samples are put on specified platforms 11b on sample tables 11. At this time, the door 33 is opened, and the first opening 2a is released. As a result, a wide opening range is assured, so that multiple plates can be put on specified positions efficiently. Also at the time of cleaning or maintenance of the inside of the housing 2, a favorable working efficiency is assured.

After completion of setting, the door 33 is shut, and the environment controller 42 is put in action. Thus, the inside of the housing 2 is kept in specified environmental conditions. Subsequently, according to the assay program of the dispensing device (not shown), the biochemical treatment is processed. In this process, the plates 6 finishing the specified culture time are taken out from the incubator 1 by the conveying device 7. Analysis, dispensing and other operations are executed in the dispensing device. Later, the plates 6 are put back into the incubator 1 by the conveying device 7. Such operation is repeated.

At this time, the plates 6 are put in and out through the second opening 2b provided in the side wall partitioning between the incubator 1 and the outside. That is, the plates 6 are put in and out by the positioning operation for moving the sample racks for positioning the platform 11b mounting the plates 6 to be discharged or an empty platform 11b for mounting the incoming plates ahead of the second opening 2b, the opening operation for opening and closing the shutter 5 for closing the second opening 11b, and the moving operation for loading and unloading the plates 6 through the second opening 11b by means of the conveying device 7. The second opening 2b has a small opening size only for passing the plates 6, and moreover only when necessary to put in and out the plates 6, the shutter 5 for closing the second opening 2b is opened automatically by the command from the controller 50. It hence minimizes the disturbance of environmental conditions due to internal environmental atmosphere flowing out or fresh air flowing into the incubator 1.

Therefore, as compared with the conventional incubator which opens the door 33 every time when putting in and out the plates 6, variations of the internal environmental conditions are extremely small, and therefore stably and highly reliable biochemical treatment quality is assured. In the embodiment, the second opening 2b is formed at the side of the housing 2, but not limited to this, for example, the second opening may be also formed in the door 33.

In the continuing process of biochemical treatment, the sample racks 10 are moved at specific timing, and the atmosphere in the incubator is agitated. This agitating operation is a combination of rotary and elevating motions of the sample racks 10. By this agitating operation, in the incubator 1 having sample racks 10 of complicated shapes combining multiple sample tables 11, the atmosphere in the incubator including gaps in the sample tables 11 can be uniformly agitated. The incubator 1 of the embodiment brings about an excellent internal agitating effect as compared with the conventional incubators using draft fans or the like. Therefore, if numerous samples are contained at the same time, dispersion of treating conditions of samples does not occur.

In the embodiment, sample racks coupling circular sample tables moved by rotating and elevating, but the invention is not limited to this example, and, for example, sample racks having simple multi-rack structure or sample racks for mounting sample containers may be also used.

As the moving device of the sample racks, moving means for making rotary and elevating motions can be used, and, for example, a moving device using a quadrature coordinate robot or multi-articulated robot may be used.

The incubator of the invention makes agitating operations to make uniform the atmosphere in the storage box by moving the sample racks. Accordingly, if the incubator has multiple layers of sample racks in complicated shape, the internal environmental condition in the incubator can be kept uniform, and the reliability of biochemical treatment is assured. The agitating operation is executed by using the drive device used for positioning of sample racks, and exclusive agitating device is not necessary. Therefore, the structure of the incubator is simplified, and the cost is reduced.

What is claimed is:

1. An incubator comprising:

a storage box, a sample rack movably disposed in said storage box, a moving device for moving said sample rack, and controller for controlling said moving device, wherein said controller has a function of selectively controlling the positioning operation for positioning the sample rack at a predetermined position and the agitating operation for agitating the atmosphere in the storage box uniformly by moving the sample rack, wherein said sample rack has a plurality of sample tables, each sample table of said plurality of sample tables is coupled vertically through a coupling member, said drive device has an elevating drive device and a rotating drive device, said elevating drive device comprises a feed screw, an elevating member slidably mounted on said feed screw, and a Z-axis motor, said rotating drive device comprises an R-axis motor, a rotating element cooperating with the R-axis motor, and a spline shaft coupled to the center of the rotating element, the plurality of sample tables are coupled to the elevating member and rotating element through the coupling members, the plurality of sample tables are moved up and down by driving of the Z-axis motor, and the plurality of sample tables rotate about the spline shaft by driving of the R-axis motor.

2. A method for making the atmosphere uniform in a storage box of an incubator comprising the steps of:

(a) supplying the incubator,
said incubator comprising the storage box, sample rack movably disposed in the storage box and moving device for moving the sample rack, (b) putting samples on said sample rack, (c) setting the atmosphere in the storage box in a predetermined environment, (d) agitating the atmosphere in the storage box by moving the sample rack, and (e) positioning the sample rack in vertical direction.

3. The method of claim 2, wherein said sample rack has a plurality of sample tables, each sample table of said plurality of sample tables is coupled vertically through a coupling member, said drive de vice has an elevating drive device and a rotating drive device, said elevating drive device comprises a feed screw, an elevating member slidably mounted on said feed screw, and a Z-axis motor, said rotating drive device comprises an R-axis motor, a rotating element cooperating with the R-axis motor, and a spline shaft coupled to the center of the rotating element, the plurality of sample tables are coupled to the elevating member and rotating element through the coupling members, at said step (d), the plurality of sample tables rotate about the spline shaft by driving of the R-axis motor, and at said step (e), the plurality of sample tables are moved up and down by driving of the Z-axis motor.

4. The method of claim 2, wherein said control device comprises a motor drive unit for moving the sample rack, a position detecting device for detecting the position of sample rack, an environment controller for controlling the atmosphere in the storage box, and a communication unit for exchanging signals with the motor drive unit, position detecting device, and environment controller, and by controlling the control device, the position of sample rack is controlled, rotation of sample rack is controlled, and atmosphere in the storage box is controlled.

5. The method of claim 2,

Wherein said sample rack includes a plurality of sample racks.

6. An incubator comprising:

a storage box, a sample rack movably disposed in said storage box, a moving device for moving said sample rack, and a controller for controlling said moving device, wherein said controller has a function of selectively controlling the positioning operation for positioning the sample rack at a predetermined position and the agitating operation for agitating the atmosphere in the storage box uniformly by moving the sample rack, wherein said moving device moves said sample rack vertically.

7. A method for making the atmosphere uniform in a storage box of an incubator comprising the steps of:

(a) supplying the incubator,
said incubator comprising the storage box, sample rack movably disposed in the storage box and moving device for moving the sample rack, (b) putting samples on said sample rack, (c) setting the atmosphere in the storage box in a predetermined environment, (d) agitating the atmosphere in the storage box by moving the sample rack, and (e) agitating said sample rack in a rotary motion, and moving said sample rack vertically.

8. A method for making the atmosphere uniform in a storage box of an incubator comprising the steps of:

(a) supplying the incubator,
said incubator comprising the storage box, sample rack movably disposed in the storage box and moving device for moving the sample rack, (b) putting samples on said sample rack, (c) setting the atmosphere in the storage box in a predetermined environment, and (d) agitating the atmosphere in the storage box by moving the sample rack, and moving of said sample rack comprises vertical movement and rotary movement.

9. A method for making the atmosphere uniform in a storage box of an incubator comprising the steps of:

(a) supplying the incubator,
said incubator comprising the storage box, sample rack movably disposed in the storage box and moving device for moving the sample rack, (b) putting samples on said sample rack, (c) setting the atmosphere in the storage box in a predetermined environment, and (d) agitating the atmosphere in the storage box by moving the sample rack, wherein said sample rack has a plurality of sample tables mutually coupled in the longitudinal direction, and at said step (d), said plurality of sample tables are moved through vertical movement and rotary movement.

* * * * *